United States Patent [19]

Anthony

[11] Patent Number: 5,044,747
[45] Date of Patent: Sep. 3, 1991

[54] MODULAR FLOW-THROUGH CELL

[75] Inventor: Michael M. Anthony, Gaithersburg, Md.

[73] Assignee: LT Industries, Rockville, Md.

[21] Appl. No.: 318,247

[22] Filed: Mar. 3, 1989

[51] Int. Cl.$^5$ .......................................... G01N 21/05
[52] U.S. Cl. ..................................... 356/246; 356/440
[58] Field of Search ............................... 356/246, 440

[56] References Cited

U.S. PATENT DOCUMENTS

| | | | |
|---|---|---|---|
| 3,515,491 | 6/1970 | Emary | 356/246 |
| 3,773,424 | 11/1973 | Selgin | 356/246 X |
| 3,886,364 | 5/1975 | Walker et al. | 356/246 X |
| 4,201,471 | 5/1980 | Pitt et al. | 356/338 X |

Primary Examiner—Davis L. Willis
Assistant Examiner—Matthew W. Koren
Attorney, Agent, or Firm—Sterne, Kessler, Goldstein & Fox

[57] ABSTRACT

A modular flow-through cell is described which has main block member having a first pathway which leads from an inlet port to a large bore and a second passageway which leads from the large bore to an outlet port. A cartridge assembly is removably inserted into the large bore to provide an optical path for light to pass through a fluid sample.

8 Claims, 3 Drawing Sheets

MODULAR FLOW-THROUGH CELL

FIELD OF THE INVENTION

This invention relates generally to a device for analyzing a liquid and more particularly to a modular flow-through cell for enabling liquid to be presented for electro-optical analysis. The invention relates also to presenting samples in solid form for electro-optical analysis.

BACKGROUND

There are a number of different devices which are used for rapid, accurate spectral analysis of the reflectivity, transflectance and/or transmitivity of a sample. One of these devices, disclosed in U.S. Pat. No 4,540,282 to Landa et al. (the Landa patent), is a device which enables immediate and rapid analysis of a number of different products. This type of device measures three generalized characteristics: the chemical constituents of the sample, the physical constituents of the sample, and the quality parameters of the sample.

The chemical constituents of a product include such things as the octane number in gasoline or the amount of aromatics in gasoline. In another environment, such parameters as the amount of protein, starch, or oil of food may be measured. In yet another environment, such blood constituents as glucose or cholesterol can be measured using such a device. In the area of pharmaceuticals, the drug composition a sample can be determined and such features as the active zones of drugs can be measured. In the tobacco industry, such chemical characteristics as nicotine, tar and menthol can be measured using such a device.

The second broad type of characteristics which can be measured using such a device are called physical parameters. Such physical parameters include characteristics such as the viscosity of liquids. In addition, such characteristics as molecular weight of a sample may be measured.

The third area which can be measured using the device as described in the Landa patent are quality parameters. Such quality parameters which may be measured by the device described in the Landa patent include such things as the taste of beers or wines. Since beer and wine each have a unique spectral signature, it may be possible to determine the quality of wine by comparing the spectral signature of a wine to be analyzed with a known product or standard. For example, once the quality of a particular wine is known, it may be possible to take a spectral signature of that wine and determine which spectral characteristics or signature wine must have in order to have a similarly good taste. Thereafter, wines need not be taste-tested in order to determine their quality. A spectral analysis only need be done and the signature be analyzed in order to determine quality.

As stated above, the device described by the Landa patent is capable of determining the spectral characteristics of a number of different products in a number of different forms.

There are basically three modes of introducing and detecting light from a sample. The first way is through reflectance. In the reflectance mode, light is introduced onto a sample. The light which is reflected is then relayed back to a detection apparatus such as the device taught by the Landa patent.

The second mode of operation is transmittance. In this mode, light is passed through a sample and the light passing through the sample is received and transmitted back to the apparatus for analyzing the light.

The third mode of operation is the transflectance mode. In this mode, light is passed through a sample. Part of the light is reflected and transmitted back to the apparatus for optically analyzing the light. The portion of the light which is not reflected passes through the sample to a mirror or other reflecting surface. The light is then passed back to the sample and again transmitted to the apparatus for analyzing the light.

In order to obtain the best results, it is necessary that the sample be in a state which allows easy and accurate access. For example, it may not always be possible to insert a light probe or the light within a stream of flowing liquid. Therefore, a part of the liquid must be tapped and run through a flow-through cell. The flowthrough cell must pass the liquid through the light stream with the stream being laminar or turbulent flow.

It is therefore an object of the invention to provide a flowthough cell which enables a sample to be readily detectable.

It is yet another object of the invention to provide a flowthrough cell with a variable optical path.

It is yet a further object of the invention to provide a flowthrough cell which is modular.

It is yet a further object of the invention to provide a flowthrough cell which enables easy access to component parts in the event that a component part is defective.

It is yet a further object of the invention to provide a compact flow-through cell.

It is yet a further object of the invention to provide a flowthrough cell which enables flow at high pressures.

It is yet a further object of the invention to provide a flowthrough cell which includes a device for heating the fluid passing therethrough.

These and other objects are achieved by the present invention.

SUMMARY OF THE INVENTION

In accordance with the purposes of the present invention as embodied and described herein, the present invention is a modular flow-through cell having a main block member. The main block member defines a first pathway leading to a large bore which traverses through the main block member. The main block member also defines a second pathway which is also in communication with the large bore. The flow-through cell of the present invention also includes a cartridge assembly for removably inserting within the large bore.

In one aspect of the invention, the cartridge assembly has means therein to ensure that flow of liquid through the flow-through cell is laminar.

In yet another aspect of the invention, the cartridge assembly has a removable spacer so that the path length of light passing through the cartridge assembly may be preselected.

In yet another aspect of the invention, a fiber optic bundle is attached to one end of the cartridge assembly for passing light through a fluid flowing through the cartridge assembly.

In yet another aspect of the invention, a mirror is provided on one end of the cartridge assembly so that light passing through a sample will be reflected back through the sample.

In yet another aspect of the invention, a magnetic sample holder is provided for enabling analysis of solid materials and the like. The magnetic holder may include a body portion which defines an aperture for passing light therethrough. The aperture has disposed around it a magnet for holding a magnetic cup.

BRIEF DESCRIPTION OF THE DRAWINGS

The accompanying drawings which are incorporated in and form a part of the specification illustrate the embodiments of the present invention and, together with the description, serve to explain the principles of the invention. In the drawings.

DETAILED DESCRIPTION OF THE PREFERRED EMBODIMENTS

Figure 1:
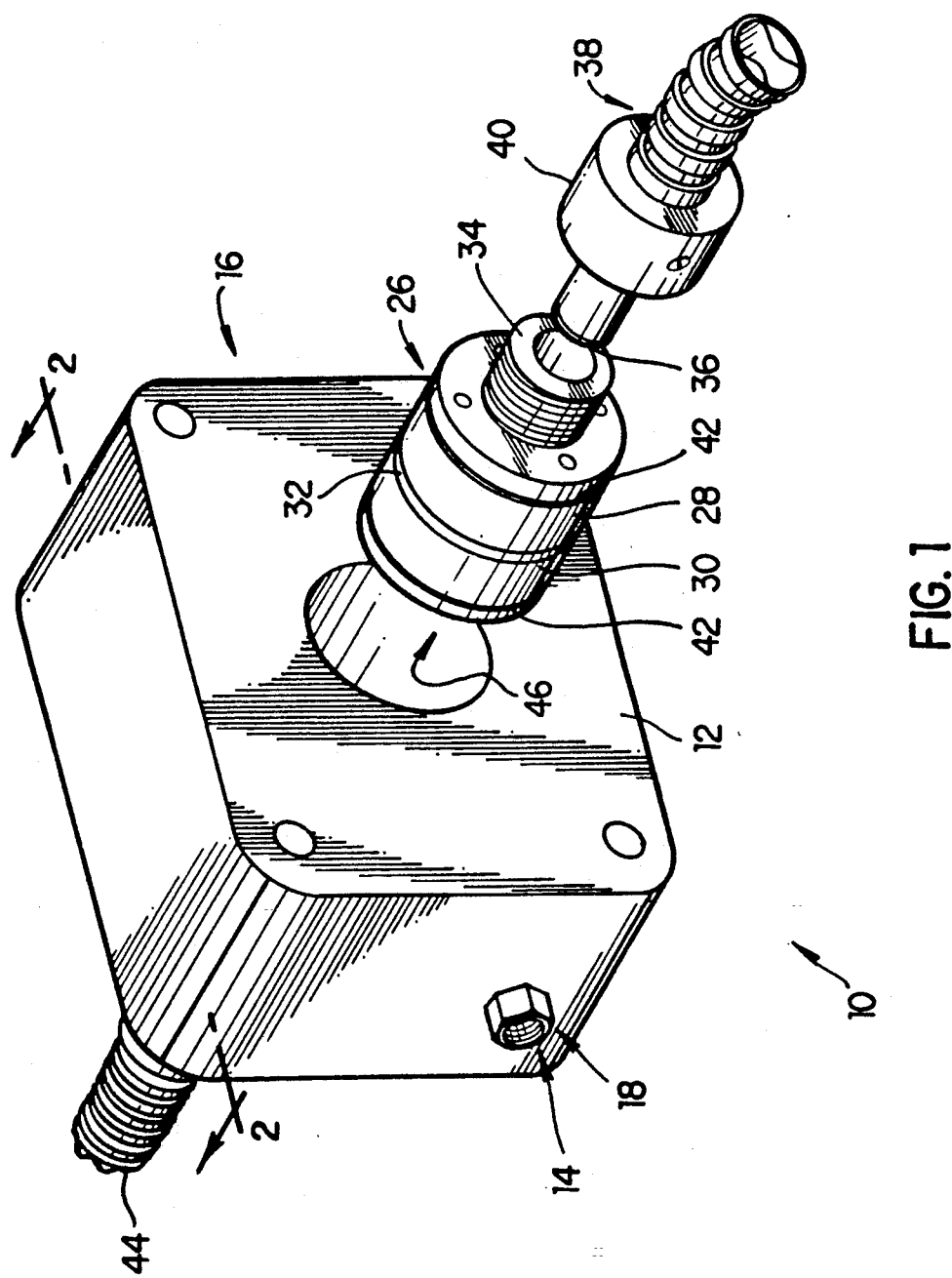
FIG. 1 is a perspective view of a flow-through cell of the present invention.

Referring first to FIG. 1, a flow-through cell is shown in conjunction with a device for introducing light into a sample. The perspective view shown in FIG. 1 shows generally a flow-through cell 10 which includes a main block member 12. Within this main block member 12 is an inlet port 14 for receiving a liquid to be analyzed with a device such as that described in the Landa et al. patent, the disclosure of which is herein incorporated by reference. The main block member 12 of flow-through cell 10 also includes an outlet port 16 which is the outlet for fluids flowing through the flow-through cell.

In general, fluid (in liquid or gas phase) which flows through inlet port 14 has been tapped off a main pipe or the like (not shown) and passes through an ancillary pipe (not shown) and into inlet port 14. The ancillary pipe (not shown) may be connected to the inlet port by means of a pipe fitting 18. Similarly, fluid exiting the outlet port 16 may pass through an ancillary pipe back to a main pipe which is flowing the liquid to be analyzed. The fluid could also for some applications, be poured into inlet port 14 via a funnel or the like.

While tapping liquid off a main pipe for analysis is one of the primary uses of a flow-through cell of the type herein described, it is anticipated that a flow-through cell of the present invention may be used in a number of different applications for a number of uses as will become obvious to those of ordinary skill in the art.

Figure 2:
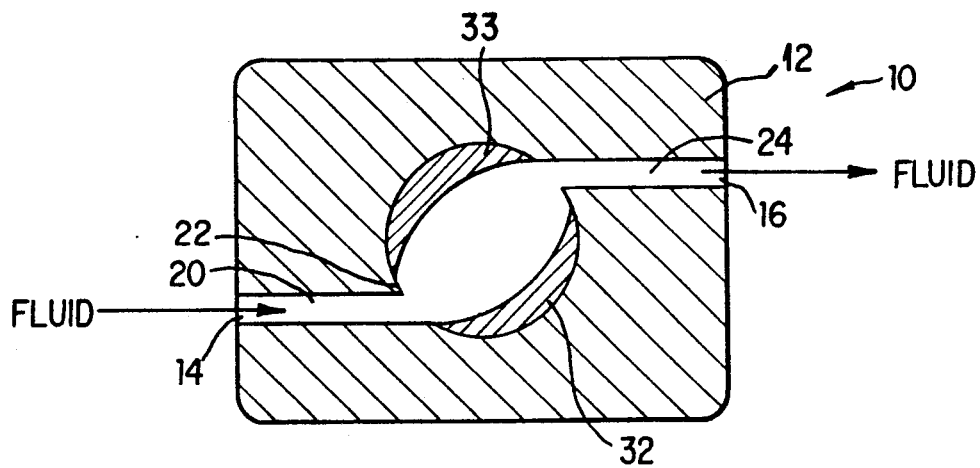
FIG. 2 is a schematic representation of a side view of FIG. 1 cut along line 2—2.

The main block member 12 of flow-through cell 10 defines a first pathway 20, seen in FIG. 2, which leads to a large bore 22 which preferably extends completely through main block member 12. The main block member 12 also defines a second pathway 24 which leads from large bore 22 through outlet port 16.

Insertable into the main block member 12 is a cartridge assembly 26. This cartridge assembly 26 is sized to fit within large bore 22 of the main block member 12. The cartridge assembly is modular in design and is designed to be removably inserted within the large bore 22.

The cartridge assembly 26 is made up of a number of component parts. In a preferred embodiment of the invention, as shown in FIG. 1, the cartridge assembly 26 may include a first cylinder 28 and a second cylinder 30. These cylinders 28, 30 are substantially the same size, thus allowing the liquid to flow substantially down the center line of the flow-through cell 10 (path shown diagrammatically in FIG. 2). Between the first cylinder 28 and the second cylinder 30 are spacers 32 and 33. In general, the spacers are coupled to first cylinder 28 or second cylinder 30 or both by dowels or the like as well as other means such as screws.

Each of the cylinders 28 and 30 are assembled with a clear optical window (not shown) which is appropriately seated with a seal to provide a leak-free assembly. This is achieved by locking the window in place with a threaded locking ring 34.

The optical windows may be made of a number of different materials. Suitable materials include quartz or sapphire. A number of other materials may also be used, preferably materials which have good optics in the near infrared range. The optical window enables light to be introduced through a sample of fluid which is passing through the flow-through cell. Light passes through the window, and through a region in which turbulent free fluid is flowing. The spacers are shaped so that they do not interfere with light passing through the flow region.

A fiber optic bundle 38 is connected to the cartridge assembly 26 by a fiber optic bundle connector 40.

In operation, fluid enters inlet port 14. The fluid then flows through the first pathway 22 and into the cartridge assembly 26. The fluid is prevented from leaking through the large bore 22 because of seals 42. These seals 42 are preferably 0-rings or the like. The fluid flows through a generally S-shaped path: through the first passageway 20, the cartridge assembly 26, and finally through the second passageway 24. The spacers 32 may be subs crescent-shaped to direct the flow so that the flow has a specific flow pattern in the optical region. By optical region, it is meant that region in which the light impinges on the fluid being analyzed.

In one mode of operation of the invention, light passes through the optical window 36. The sample passing through the flow-through cell reflects the light back through fiber optic bundle 38. In this mode, a bidirectional fiber optics bundle is used which passes light in two directions simultaneously.

In a second mode of operation of the invention, light from fiber optic bundle 38 is passed through optical window 36. The light passes through the sample and is received by a second fiber optic bundle 44 (see FIG. 1). The second fiber optic bundle 44 then transmits the light to be analyzed to a device such as that described in the Landa et al. patent. This mode of operation is called the transmittance mode.

In yet another embodiment of the invention, a reflector is placed at the end 46 of cartridge assembly 26. This reflector may replace an optical window associated with bundle 44 used in the second mode, and is used to reflect light which has previously passed through the sample. The light is reflected back through the sample and received by fiber optic bundle 38, which transmits the light to a device such as that taught by the Landa et al. patent. The light is then analyzed and a spectral signature is obtained.

Referring again to FIG. 2, one of the advantages of the present invention is that the optical path of the light can be varied. This can be done simply by replacing the spacers 32 with spacers having a greater thickness. This is easily done, can be done in a short period of time, and can be done on site.

In order to ensure that the cartridge 26 is positioned properly within the large bore 22, an indent is placed on the cartridge 26 which lines up with a set screw on the main block member 12. Naturally, other devices and methods for ensuring that the cartridge assembly 26 is properly positioned are contemplated by the present invention.

In other aspect of the invention, the flow-through cell 10 can be heated either by inserting electrical plugs or putting heat passages such as hot water passages, hot liquid passages or hot gas passages in the main block member 12 of flow-through cell 10 in any desired configuration. The purpose for heating the flow-through cell 10 is to maintain the sample at a substantially constant temperature. It may be that the fluid is flowing in a pipe of varying temperature or at a temperature which is not optimal for determining certain characteristics. The flow-through cell of the present invention enables the liquid to be tapped and run through the flow-through cell at a temperature which provides optimal conditions. One example of a liquid which should be heated in order to obtain the best results is milk. Milk is a medium that requires the maintenance of extremely precise temperatures to obtain the kind of measurements which are required.

Another advantage of the invention is that the flow-through cell enables products to be analyzed at a remote location. This may be valuable if the liquid to be analyzed is explosive or the like. The above-described flow-through cell can operate at high pressures and temperatures. For example, it may operate at pressures up to 150 psi, and will take fluids of temperatures up to 100° C. or higher.

Figure 3:
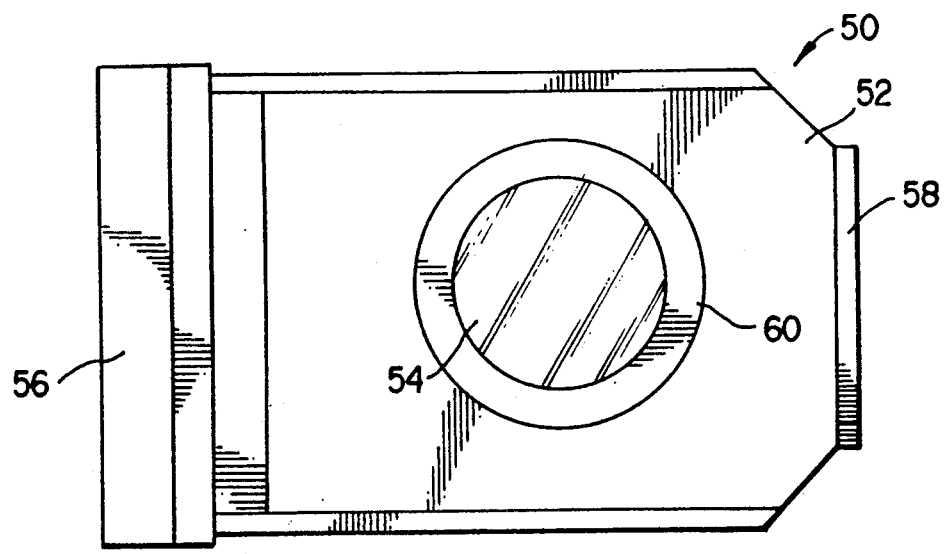
FIG. 3 is a front view of a magnetic holder of the present invention.
Figure 4:
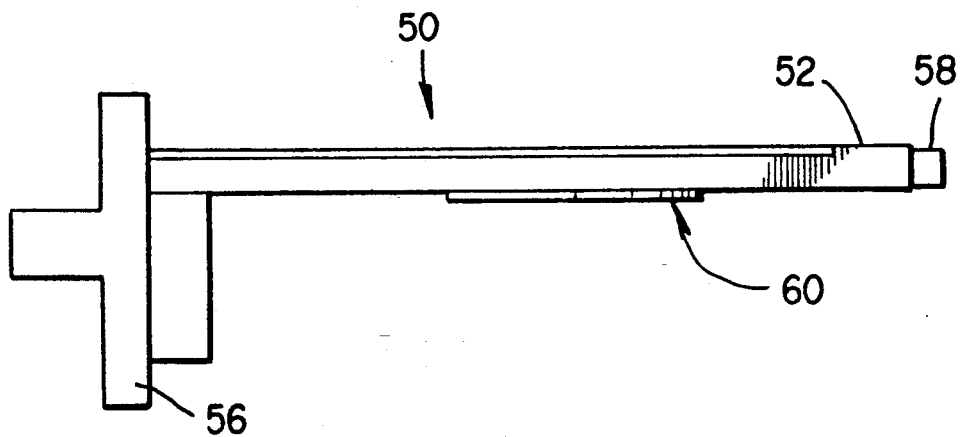
FIG. 4 is a side view of a magnetic holder of the present invention.

While the above-describe flow-through cell 10 provides a superior device for presenting liquids and gases for analysis, it is not specifically designed for the presentation of solid materials. A device for properly presenting solid materials to be analyzed is depicted in FIGS. 3 and 4. In this embodiment of the invention, a magnetic sample holder 50 includes a body portion 52 which is made of a material such as stainless steel or the like. It should be noted, however, that a number of different materials may be used depending on the particular application.

The body portion 52 defines an opening in which a window 54 is placed. The window is made of quartz, or any other optically suitable material such as sapphire. On one end of body 52 is a flange 56 which enables easy insertion of the entire magnetic sample holder 50 into a suitable frame for holding the sample holder in the stream of light. When the magnetic sample holder 50 is inserted into the suitable frame (not shown), a beam of light is directed through window 54 and is either reflected by or transmitted through the solid sample as will be described below.

At the end of the body portion 52 which is opposite the side of the body portion which has flange 56, a magnet 58 is provided which is attracted to a magnet within the suitable frame described above. The magnet 58 helps to stabilize the magnetic sample holder 50 within the suitable frame.

Figure 5:
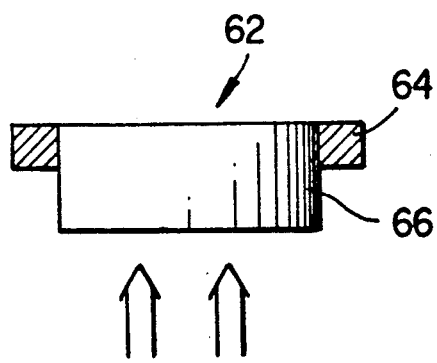
FIG. 5 is a schematic representation of a magnetic cup for use with the magnetic holder of the present invention.

An inventive aspect of this invention is the use of a magnetic device to maintain proper orientation and packing pressure of a sample cup 62 (shown in FIG. 5 by itself). In a preferred embodiment of the invention, a ring magnet 60 is placed around the periphery of window 54. This magnet makes it possible to simply place the sample cup 62 having a corresponding magnet 64 over window 54. The ring magnet 60 holds the sample cup 62 in place. A sample, such as a solid powder or the like, is placed within the interior 66 of cup 62.

In operation, magnetic cup 62 is filled with a solid material and is placed over the window 54. The magnetic cup 62 is held in place by magnets 60 and 64 on the magnetic sample holder and on the magnetic cup, respectively. The entire magnetic sample holder assembly is then inserted into a suitable frame (not shown). In this way, light may be introduced to and retrieved from the sample via appropriate means such as a fiber optic bundle.

The foregoing description of the preferred embodiments of the invention have been presented for purposes of illustration and description. It is not intended to be exhaustive or to limit it to the precise form disclosed. Obviously, many modifications and variations may be made in light of the above teachings. For example, the flow-through cell has been described in particular reference to the flowing of liquids. It may, however, be used in conjunction with solids or an adaptation thereof may be used with solids. Obviously, many modifications and variations may be made in light of the above teachings.

The embodiments were chosen and described in order to best explain the principles of the invention and its practical application to thereby enable others skilled in the art to best utilize the invention in various embodiments and with various modifications as are suited to the particular use contemplated. As previously described, the invention may be used in a number of different environments with a number of different samples in different phases. As such, each application may require somewhat different materials. For example, it may be necessary to use materials other than a rubber O-ring on the flow-through cell if it is being used in an extremely harsh environment. Similarly, the materials may be chosen which are best suited for a particular application. Many other modifications and variations are contemplated without drifting from the spirit of the present invention. It is intended that the scope of the invention be defined by the claims appended hereto.

We claim:

1. A modular flow-through cell, comprising
   (a) a main block member, said main block member having a first fluid passageway extending from an inlet port, a second fluid passageway extending from an outlet and a bore, said first and second fluid passageways being in fluid communication with said bore;
   (b) a cartridge assembly removably disposed within said bore, said cartridge assembly having an optical window for receiving light therethrough and having means for altering fluid flow within said cartridge assembly, and wherein fluid entering said inlet port will exit said exit port and will pass in a location to receive light passing through said optical window, whereas said cartridge assembly is removable from said cell without disassembly thereof.

2. The modular flow-through cell of claim 1, wherein said cartridge assembly includes a seal for preventing liquid from flowing therearound.

3. The modular flow-through cell of claim 2, wherein said seal is an O-ring.

4. The modular flow-through cell of claim wherein said cartridge comprises a first cylinder, a second cylinder, and a spacer disposed between said first and second cylinder.

5. The modular flow-through cell of claim 4, wherein said spacer is removable from between said first and second cylinders.

6. The modular flow-through cell of claim 3, wherein said cartridge further comprises means to attach a fiber optic cable thereto.

7. The modular flow-through cell of claim wherein the longitudinal axis of the first fluid passageway and the longitudinal axis of the second fluid passageway are not co-linear.

8. The modular flow-through cell of claim 1, further comprising means to reflect light passing through a sample.

* * * * *